United States Patent
Pruvost et al.

(10) Patent No.: US 11,203,736 B2
(45) Date of Patent: Dec. 21, 2021

(54) METHOD FOR THE CULTURE OF PHOTOSYNTHETIC ORGANISMS USING A CO2 SOURCE

(71) Applicants: UNIVERSITE DE NANTES, Nantes (FR); CENTRE NATIONAL DE LA RECHERCHE SCIENTIFIQUE, Paris (FR)

(72) Inventors: Jérémy Pruvost, Saint Brevin les Pins (FR); Benjamin Le Gouic, Guerande (FR)

(73) Assignees: UNIVERSITE DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 258 days.

(21) Appl. No.: 16/075,943

(22) PCT Filed: Feb. 22, 2017

(86) PCT No.: PCT/FR2017/050393
§ 371 (c)(1),
(2) Date: Aug. 6, 2018

(87) PCT Pub. No.: WO2017/144817
PCT Pub. Date: Aug. 31, 2017

(65) Prior Publication Data
US 2020/0263120 A1    Aug. 20, 2020

(30) Foreign Application Priority Data
Feb. 24, 2016 (FR) ..................................... 16/51516

(51) Int. Cl.
| | | |
|---|---|---|
| C12M 1/34 | (2006.01) | |
| C12M 1/107 | (2006.01) | |
| C12N 1/12 | (2006.01) | |
| C12N 1/20 | (2006.01) | |

(52) U.S. Cl.
CPC ............ *C12M 41/34* (2013.01); *C12M 23/36* (2013.01); *C12M 41/26* (2013.01); *C12N 1/12* (2013.01); *C12N 1/20* (2013.01)

(58) Field of Classification Search
CPC ..................................................... C12M 23/36
See application file for complete search history.

(56) References Cited

U.S. PATENT DOCUMENTS

| 9,453,193 B2 | 9/2016 | Babbitt et al. |
| 2014/0186931 A1 | 7/2014 | Gonzales et al. |

FOREIGN PATENT DOCUMENTS

| WO | 2010/108049 A1 | 9/2010 |
| WO | 2012/056126 A1 | 5/2012 |
| WO | 2014/063229 A1 | 5/2014 |

OTHER PUBLICATIONS

Laws et al. Biotechnology and Bioengineering, 1991, 37:936-3947.*
Granum et al., "A photobioreactor with pH control: demonstration by growth of the marine diatom Skeletonema costatum", Journal of Plankton Research, 2002, pp. 557-563, vol. 24, No. 6.
McGinn et al., "Integration of microalgae cultivation with industrial waste remediation for biofuel and bioenergy production: opportunities and limitations", Photosynthesis Research, 2011, pp. 231-247, vol. 109, No. 1-3.
Garcia et al., "Minimization of carbon losses in pilot-scale outdoor photobioreactors by model-based predictive control", Biotechnology and Bioengineering, 2003, pp. 533-543, vol. 84, No. 5.
Berenguel et al., "Model predictive control of pH in tubular photobioreactors", Journal of Process Control, pp. 377-387, vol. 14, vol. 4, 2004.
Han et al., "Enhanced lipid productivity ofChlorella pyrenoidosathrough the culture strategy of semi-continuous cultivation with nitrogen limitation and pH control by CO2", Bioresource Technology, pp. 418-424, vol. 136, 2013.
International Search Report, dated May 10, 2017, from corresponding PCT application No. PCT/FR2017/050393.

* cited by examiner

*Primary Examiner* — Bin Shen
(74) *Attorney, Agent, or Firm* — Nixon & Vanderhye

(57) ABSTRACT

Disclosed is a method for the culture of photosynthetic organisms selected from among microalgae, cyanobacteria and macroalgae using a continuous or discontinuous CO2 source.

12 Claims, 1 Drawing Sheet

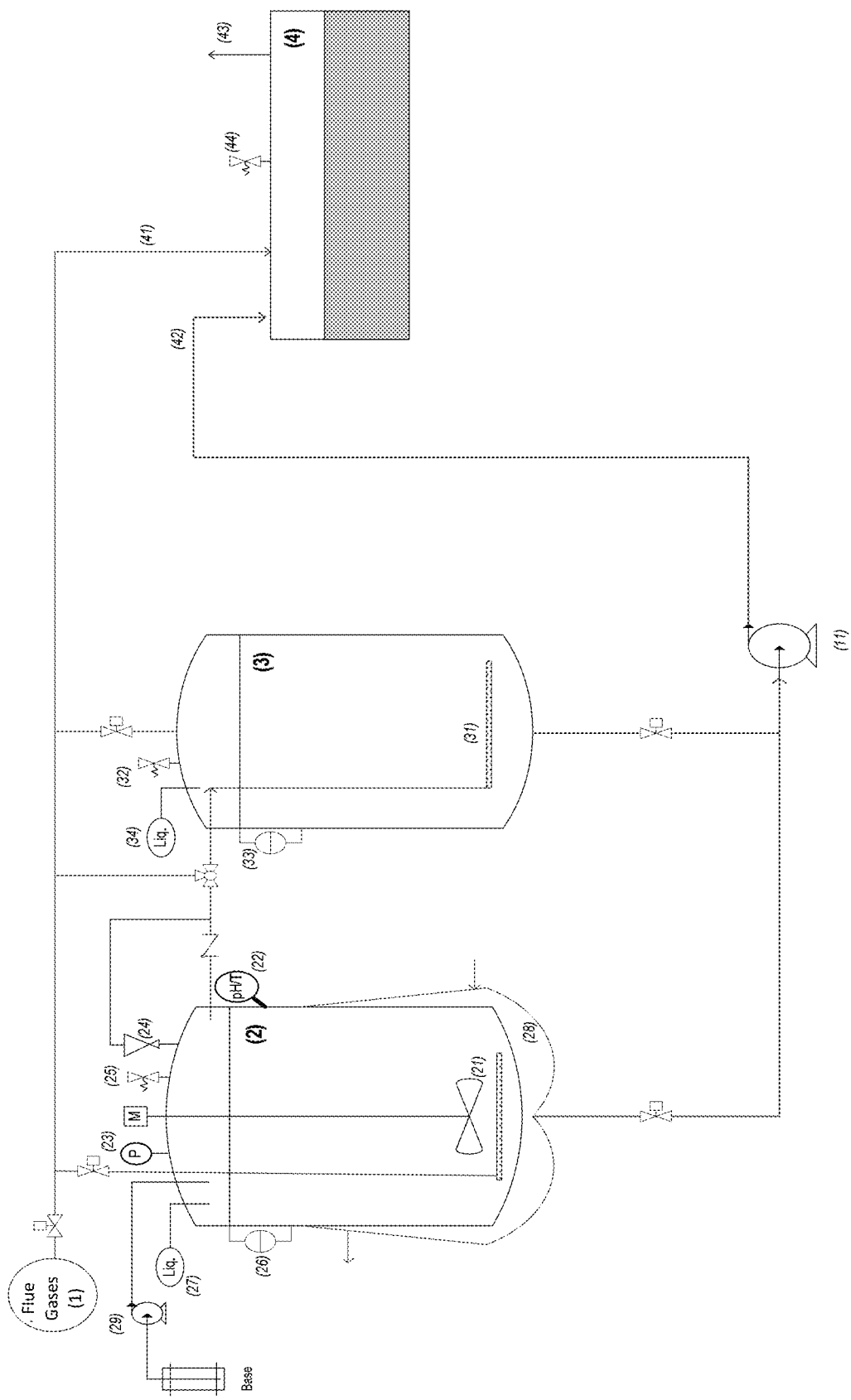

US 11,203,736 B2

METHOD FOR THE CULTURE OF PHOTOSYNTHETIC ORGANISMS USING A CO2 SOURCE

This application is a 371 of international application PCT/FR2017/050393, filed Feb. 22, 2017.

The present invention relates to a method for the culture of photosynthetic organisms using a continuous or discontinuous $CO_2$ source.

Microalgae and cyanobacteria are single-cell photosynthetic microorganisms that are capable of producing different types of organic materials, such as proteins, carbohydrates and lipids, and are considered to be optimal organisms for obtaining high-value-added products, such as functional polysaccharides, carotenoids, vitamins, unsaturated fatty acids, etc.

With regard to macroalgae, their nutritional value means that the culture thereof is of particular interest.

In addition, during the culture of microalgae, cyanobacteria and macroalgae, there is a consumption and thus elimination of carbon dioxide, which is the main factor in respect of global warming. These photosynthetic organisms have a much shorter multiplication time compared to land plants (and therefore the amount of carbon dioxide can be efficiently reduced), grow quickly in a poor environment, and can directly utilise the combustion gases originating from power stations or factories.

In order to efficiently eliminate carbon dioxide whilst producing microalgae, cyanobacteria and macroalgae and/or compounds of interest at high yields, it is necessary to provide installations making it possible to adapt to intermittent sources of carbon dioxide, because it is in this form that carbon dioxide is usually released into the atmosphere.

Currently, the gaseous effluent is especially injected directly into the culture system, where it is transferred to the liquid culture phase. During periods in which the intermittent production source has ceased, the culture consumes the residual dissolved carbon, which can lead to restricted growth if the dissolved carbon becomes insufficient.

The gaseous effluent can also be injected into a liquid solution upstream of the system so as to form a carbonated solution, which is then used to feed the culture system. This makes it possible to provide a source of dissolved carbon during periods in which the source has ceased. Nevertheless, the considerable dissolution of the carbon means working at a high pH, which is incompatible with the pH regulation of the culture system, because this requires an acidic source since the consumption of the dissolved carbon by the microalgae growth basifies the medium.

One object of the present invention is thus to provide a method making it possible to achieve optimal culture of photosynthetic organisms with an intermittent source of gaseous $CO_2$.

A further object of the present invention is to provide a method making it possible to reconcile the ongoing needs of systems for the culture of photosynthetic organisms with regard to the supply of dissolved carbon and pH regulation, with an intermittent source of gaseous $CO_2$.

Consequently, the invention relates to the use of a first aqueous composition having a pH greater than $pH_H$ and of a second composition having a pH lower than $pH_B$ for the culture of photosynthetic organisms, selected from microalgae, cyanobacteria and macroalgae, in a culture system comprising a culture medium, in which:

said first aqueous composition having a pH greater than $pH_H$ is obtained by contacting $CO_2$ produced by a continuous or discontinuous $CO_2$ source, a base, water and possibly all or some of the constituents of an algal culture medium;

the second aqueous composition having a pH lower than $pH_B$ is obtained by dissolving $CO_2$ produced by said source in water or an aqueous solution containing all or some of the constituents of an algal culture medium;

the pH of said culture medium being such that:

when the pH of said culture medium reaches an upper limit, $pH_H$, the second aqueous composition and/or $CO_2$ produced by said source are/is added to said culture medium so as to lower the pH, preferably until the pH of said culture medium reaches a lower limit, $pH_B$;

when the pH of said culture medium reaches said lower limit, $pH_B$, the first aqueous composition is added to said culture medium so as to raise the pH, preferably until the pH of said culture medium reaches an intermediate value, $pH_I$, with $pH_B < pH_I < pH_H$; and possibly, when the pH of said culture medium is lower than $pH_H$, especially lower than $pH_1$, the first aqueous composition is added to said culture medium so as to raise the pH, especially until the pH of said culture medium reaches the intermediate value $pH_I$.

Surprisingly, the use according to the present invention of the two aqueous compositions makes it possible to satisfy the ongoing needs of systems for the culture of photosynthetic organisms with regard to the supply of dissolved carbon whilst allowing a regulation of the pH, this all being possible even with an intermittent source of gaseous $CO_2$.

The term "microalgae" means microscopic algae.

The term "cyanobacteria" means bacteria from the phylum Cyanobacteria, from the class of Cyanophyceae.

The term "macroalgae" means large algae or giant algae, that is to say algae larger than microalgae.

The term "$CO_2$ source" means a source producing $CO_2$, especially in gaseous form, or a composition, especially a gaseous composition, comprising $CO_2$, especially in gaseous form.

This source can be continuous, that is to say it delivers the $CO_2$ at a rate not equal to zero, over a given period, for example an hour, day, or a week.

Especially, this flow not equal to zero is constant.

Alternatively, the source can be discontinuous, that is to say sometimes delivers $CO_2$ at a rate not equal to zero, and sometimes does not produce $CO_2$, over a given period, for example an hour, a day, or a week.

The term "algal culture medium" means a medium enabling the culture of said photosynthetic organisms.

In addition to said photosynthetic organisms selected from microalgae, cyanobacteria and macroalgae, that is to say the algal biomass, the culture medium comprises constituents allowing the growth of said photosynthetic organisms and/or the production of molecules of interest by said photosynthetic organisms.

The culture medium is for example composed of water, elements that are nutritive for the photosynthetic organisms, for example mineral salts—such as nitrates, ammonium, phosphates, sulphates and metals of the iron or magnesium type, etc.—, carbonated ions, or organic elements of the sugar type.

The term "$pH_H$" means the upper limit of the pH of the culture medium. $pH_H$ is defined especially so as to be compatible with the physiology of the photosynthetic organism placed in culture. Thus, $pH_H$ can be a value above which the growth of said photosynthetic organisms and/or the production of molecules of interest by said photosynthetic organisms is no longer optimal.

The term "$pH_B$" means the lower limit of the pH of the culture medium. $pH_B$ is especially defined so as to be compatible with the physiology of the photosynthetic organism placed in culture. Thus, $pH_B$ can be a value below which the growth of said photosynthetic organisms and/or the production of molecules of interest by said photosynthetic organisms is no longer optimal.

$pH_B$ and $pH_H$ flank $pH_I$. This intermediate value is especially the pH allowing optimal growth of said photosynthetic organisms and/or optimal production of molecules of interest.

The term "first aqueous composition" means a composition comprising water, especially an aqueous solution, having a pH greater than $pH_H$.

The first aqueous composition possibly comprises all or some of the constituents of an algal culture medium as defined further above.

This first aqueous composition comprises carbonate ions and bicarbonate ions, the carbonate and bicarbonate ions being especially the most dominant carbonated species in that case.

The dissolved inorganic carbon (DIC) especially comprises carbonate ions, bicarbonate ions and carbonic acid.

In the first aqueous composition, the DIC is predominantly in the form of carbonate ions and bicarbonate ions.

Said base makes it possible to increase the pH of the first aqueous composition and the concentration of DIC.

For example, in the case of an industrial flue gas comprising 9% $CO_2$ at 25° C., the pH and DIC are related as indicated in the following table:

| pH | DIC (mM) |
|---|---|
| 7.5 | 46.7 |
| 8 | 141.2 |
| 8.5 | 444.1 |
| 9 | 1441.2 |

The term "second aqueous composition" means a composition comprising water, especially an aqueous solution, having a pH lower than $pH_B$.

The second aqueous composition possibly comprises all or some of the constituents of an algal culture medium as defined further above.

This second aqueous composition comprises carbonic acid, the carbonic acid being especially the dominant carbonated species in that case.

In the second aqueous composition, the DIC is predominantly in the form of carbonic acid.

For example, in the case of an industrial flue gas comprising 9% $CO_2$ at 25° C., the pH of the second aqueous composition, at equilibrium, is 4.42 and the concentration of DIC is 3 mM.

In accordance with an advantageous embodiment, the invention relates to a use as defined above, in which the photosynthetic organisms are selected from the group composed of:
- microalgae, especially microalgae of the genera *Chlorella*, *Nannochloropsis*, *Chlamydomonas*, *Tetraselmis*, *Scendesmus*, *Parachlorella*, *Porphyridium*, *Botryococcus* and *Neochloris*;
- cyanobacteria, especially of the genera *Arthrospira*, *Aphazomenon* and *Synechocystis*; and
- macroalgae, especially the macroalgae Ulva, Fucus, Palmaria.

The genus of cyanobacteria *Arthrospira* is commonly known as *spirulina*.

In accordance with an advantageous embodiment, the invention relates to a use as defined above, in which the $CO_2$ source is formed by industrial flue gases, said $CO_2$ source being selected especially from the group formed by emissions from boilers, thermal power plants, cement plants, metallurgy plants, refineries, factories manufacturing ammonia, fermentation processes, and anaerobic digestion processes.

In accordance with an advantageous embodiment, the invention relates to use as defined above, in which the value of $pH_I$ in the culture medium is between 6 and 10.

In accordance with an advantageous embodiment, the invention relates to a use as defined above, in which $pH_I$ is the optimal pH for growth of said photosynthetic organisms in the culture medium.

In accordance with an advantageous embodiment, the invention relates to a use as defined above, in which $pH_H$ in the culture medium is such that $pH_H=pH_I+x$, x being between 0.02 and 1.5, especially between 0.1 and 0.2.

In accordance with an advantageous embodiment, the invention relates to a use as defined above, in which $pH_B$ in the culture medium is such that $pH_B=pH_I-y$, y being between 0.02 and 1.5, especially between 0.1 and 0.2.

In accordance with an advantageous embodiment, the invention relates to a use as defined above, in which said base is selected from the group composed of sodium hydroxide and potassium hydroxide.

In accordance with an advantageous embodiment, the invention relates to a use as defined above, in which the temperature of the culture medium is between 15° C. and 35° C.

In accordance with an advantageous embodiment, the invention relates to a use as defined above, in which the culture system is a closed system.

The term "closed culture system" means a culture area that is isolated from its external environment, for example by a transparent material so as to allow light to pass through. This system makes it possible to better control the culture conditions, and especially the supply of carbon, and to prevent external contamination by other organisms. This leads ultimately to an increased productivity of a biomass and improved quality.

In accordance with an advantageous embodiment, the invention relates to a use as defined above, in which the culture system is an open system.

The term "open culture system" means a culture system open to the ambient environment. The benefit is that it is a less costly system compared to closed systems.

The invention also relates to a method for the culture of photosynthetic organisms, selected from microalgae, cyanobacteria and macroalgae, using a continuous or discontinuous $CO_2$ source, in which the $CO_2$ is directed by means of pipes and valves controlled preferably by an automaton:
- in a culture system comprising a medium for the culture of photosynthetic organisms; and/or
- in water or an aqueous solution containing all or some of the constituents of an algal culture medium so as to obtain, in the presence of a base, a first aqueous composition having a pH greater than $pH_H$; and/or
- in water or an aqueous solution containing all or some of the constituents of an algal culture medium so as to obtain a second aqueous composition having a pH lower than $pH_B$, by dissolving $CO_2$ produced by said source in water;

said method being characterised in that, during the culture of photosynthetic organisms in said culture medium, in order to obtain a biomass of photosynthetic organisms using the $CO_2$ originating from said source and/or the carbonate ions and the carbonic acid respectively contained in the first and second aqueous compositions:
i. when the pH of said culture medium reaches an upper limit, $pH_H$, the second aqueous composition and/or the $CO_2$ produced by said source are/is added to said culture medium in order to lower the pH, preferably until the pH of said culture medium reaches a lower limit, $pH_B$;
ii. when the pH of said culture medium reaches said lower limit, $pH_B$, the first aqueous composition is added to said culture medium so as to increase the pH, preferably until the pH of said culture medium reaches an intermediate value, $pH_I$, with $pH_B<pH_I<pH_H$; and
iii. possibly, when the pH of said culture medium is lower than $pH_H$, especially lower than $pH_I$, the first aqueous composition is added to said culture medium so as to increase the pH, especially until the pH of said culture medium reaches the intermediate value $pH_I$.

Generally, the consumption of the carbon dissolved in the culture medium by the photosynthetic organisms currently growing causes the pH of said culture medium to rise.

For example, under consideration of a culture medium being at $pH_I$ at a given moment, the pH will rise during the course of growth of the photosynthetic organisms. When the pH has reached $pH_H$, the action i will be performed up to $pH_B$. Then, step ii will be performed, preferably up to $pH_I$, this sequence being repeated as necessary.

The action iii can be performed in the following case: when the pH of the culture medium is between $pH_B$ and $pH_I$, the action iii can be performed, preferably up to $pH_I$. The pH will then rise during the course of the growth of the photosynthetic organisms, up to $pH_H$. The action i will then be performed up to $pH_B$. Step ii will then be performed, preferably up to $pH_I$, this sequence being repeated as necessary.

Instead of waiting for the pH of the medium to rise to $pH_H$ due to the consumption of the carbon dissolved in the culture medium by the photosynthetic organisms currently growing, it is also possible to perform the action iii.

For example, under consideration of a culture medium being at $pH_I$ at a given moment, the action iii can be performed up to $pH_H$, then step i can be performed up to $pH_B$, and then step ii up to $pH_I$, and so on.

In accordance with an advantageous embodiment, the invention relates to a method as defined above, in which the photosynthetic organisms are selected from the group formed by:
microalgae, especially microalgae of the genera *Chlorella*, *Nannochloropsis*, *Chlamydomonas*, *Tetraselmis*, *Scendesmus*, *Parachlorella*, *Porphyridium*, *Botryococcus* and *Neochloris*;
cyanobacteria, especially of the genera *Arthrospira*, *Aphazomenon* and *Synechocystis*; and
macroalgae, especially the macroalgae Ulva, Fucus, Palmaria.

In accordance with an advantageous embodiment, the invention relates to a method as defined above, in which the $CO_2$ source is formed by industrial flue gases, said $CO_2$ source being selected especially from the group composed of emissions from boilers, thermal power plants, cement plants, metallurgical plants, refineries, factories manufacturing ammonia, fermentation processes, and anaerobic digestion processes.

In accordance with an advantageous embodiment, the invention relates to a method as defined above, in which the $CO_2$ source is discontinuous and the automaton acts on the various valves connecting a system for the culture of photosynthetic organisms comprising said culture medium, the first aqueous composition having a pH greater than $pH_H$ and the second composition having a pH lower than $pH_B$, such that:
when the $CO_2$ source produces $CO_2$:
$CO_2$ is directed into water or an aqueous solution containing all or some of the constituents of an algal culture medium so as to obtain said first aqueous composition in the presence of a base, and is directed into water or an aqueous solution containing all or some of the constituents of an algal culture medium so as to obtain said second aqueous composition by dissolving $CO_2$ produced by said source in the water or the aqueous solution;
(if desired) $CO_2$ is directed directly into the culture system if the pH is such that $pH_B<pH<pH_H$;
when the pH of said culture medium reaches an upper limit, $pH_H$, $CO_2$ produced by said source and possibly the second aqueous composition are added to said culture medium so as to lower the pH, preferably until the pH of said culture medium reaches a lower limit, $pH_B$;
when the pH of said culture medium reaches said lower limit, $pH_B$, the $CO_2$ produced by said source is no longer added to said culture medium, and, if desired, the first aqueous composition is added to said culture medium so as to raise the pH, preferably until the pH of said culture medium reaches an intermediate value, $pH_I$, with $pH_B<pH_I<pH_H$;
when the $CO_2$ source does not produce $CO_2$:
the first aqueous composition is added to the culture medium so as to supply dissolved carbon to said culture medium, resulting in an increase of the pH until preferably the pH of said culture medium reaches an intermediate value, $pH_I$, with $pH_B<pH_I<pH_H$;
when the pH of said culture medium reaches an upper limit, $pH_H$, the second aqueous composition is added to said culture medium so as to lower the pH, preferably until the pH of said culture medium reaches a lower limit, $pH_B$.

The two actions described when the $CO_2$ source does not produce $CO_2$ can be swapped. In other words, there is generally no defined order. Moreover, these actions can be repeated as necessary.

In accordance with advantageous embodiment, when the $CO_2$ source does not produce $CO_2$:
the first aqueous composition is added to the culture medium so as to supply dissolved carbon to said culture medium, resulting in an increase of the pH until preferably the pH of said culture medium reaches an intermediate value, $pH_I$, with $pH_B<pH_I<pH_H$; then
when the pH of said culture medium reaches an upper limit, $pH_H$, the second aqueous composition is added to said culture medium so as to lower the pH, preferably until the pH of said culture medium reaches a lower limit, $pH_B$.

Especially, between the two actions mentioned above, the pH rises, especially from $pH_I$, to $pH_H$ due to the consumption of dissolved carbon in the culture medium by the photosynthetic organisms currently growing.

In accordance with an advantageous embodiment, when the $CO_2$ source does not produce $CO_2$:
- when the pH of said culture medium reaches an upper limit, $pH_H$, the second aqueous composition is added to said culture medium so as to lower the pH, preferably until the pH of said culture medium reaches a lower limit, $pH_B$; then
- the first aqueous composition is added to the culture medium so as to supply dissolved carbon to said culture medium, resulting in an increase of the pH until preferably the pH of said culture medium reaches an intermediate value, $pH_I$, with $pH_B < pH_I < pH_H$.

Especially, the pH rises before the first action mentioned above, up to $pH_H$, due to the consumption of the dissolved carbon in the culture medium by the photosynthetic organisms currently growing. The first and second actions then follow.

In accordance with an advantageous embodiment, the invention relates to a method as defined above, in which the value of $pH_I$ in the culture medium is between 6 and 10.

In accordance with an advantageous embodiment, the invention relates to a method as defined above, in which $pH_I$ is the optimal pH for growth of said photosynthetic organisms in the culture medium.

In accordance with an advantageous embodiment, the invention relates to a method as defined above, in which $pH_H$ in the culture medium is such that $pH_H = pH_I + x$, x being between 0.02 and 1.5, especially between 0.1 and 0.2.

In accordance with an advantageous embodiment, the invention relates to a method as defined above, in which $pH_B$ in the culture medium is such that $pH_B = pH_I - y$, y being between 0.02 and 1.5, especially between 0.1 and 0.2.

In accordance with an advantageous embodiment, the invention relates to a use as defined above, in which said base is selected from the group composed of sodium hydroxide and potassium hydroxide.

In accordance with an embodiment, the pH of the first aqueous composition can be between 7.5 and 9.

In accordance with an embodiment, the concentration of DIC in the first aqueous composition can be between 45 and 1450 mM.

In accordance with an embodiment, the pH of the second aqueous composition, at equilibrium, can be between 4 and 5, and is especially approximately 4.4.

In accordance with an embodiment, the concentration of carbonic acid in the second aqueous composition can be between 1 and 5 mM, and especially is approximately 3 mM.

In accordance with an advantageous embodiment, the invention relates to a method as defined above, in which the temperature of the culture medium is between 15° C. and 35° C.

In accordance with an advantageous embodiment, the invention relates to a method as defined above, in which the culture system is a closed system.

The term "closed culture system" means a culture area that is isolated from its external environment, for example by a transparent material so as to allow light to pass through. This system makes it possible to better control the culture conditions, and especially the supply of carbon, and to prevent external contamination by other organisms. This leads ultimately to an increased productivity of a biomass and improved quality.

In accordance with an advantageous embodiment, the invention relates to a method as defined above, in which the culture system is an open system.

The term "open culture system" means a culture system open to the ambient environment. The benefit is that it is a less costly system compared to closed systems.

The invention also relates to a device for the culture of photosynthetic organisms, selected from microalgae, cyanobacteria and macroalgae, using a continuous or discontinuous $CO_2$ source, comprising the following elements:
- a means A for capturing $CO_2$ produced by said source, said means comprising water or an aqueous solution containing all or some of the constituents of an algal culture medium, and a base, and making it possible to obtain a first aqueous composition having a pH greater than $pH_H$;
- a means B for capturing $CO_2$ produced by said source, said means comprising water or an aqueous solution containing all or some of the constituents of an algal culture medium and making it possible to obtain a second aqueous composition having a pH lower than $pH_B$;
- a system for the culture of said photosynthetic organisms, equipped with means for measuring pH;
- pipes and valves connecting the $CO_2$ source, the system for the culture of said photosynthetic organisms, and the means A and B;
- a system for controlling and regulating gaseous and liquid flows between the $CO_2$ source, the system for the culture of said photosynthetic organisms, and the means A and B, preferably an automaton, characterised in that the control system is designed such that:
  - the $CO_2$ produced by said source is directed towards said culture system and/or said means A and B for capturing $CO_2$;
  - when the pH of said culture medium reaches an upper limit, $pH_H$, the second aqueous composition originating from the means B and/or $CO_2$ produced by said source are added to said culture medium so as to lower the pH, preferably until the pH of said culture medium reaches a lower limit, $pH_B$;
  - when the pH of said culture medium reaches said lower limit, $pH_B$, the first aqueous composition originating from the means A is added to said culture medium so as to increase the pH, preferably until the pH of said culture medium reaches an intermediate value, $pH_I$, with $pH_B < pH_I < pH_H$; and
  - possibly, when the pH of said culture medium is lower than $pH_H$, especially lower than $pH_I$, the first aqueous composition is added to said culture medium so as to increase the pH, especially until the pH of said culture medium reaches the intermediate value $pH_I$.

The means A is for example a carbonation tank, comprising water or an aqueous solution containing all or some of the constituents of an algal culture medium, and a base, in which $CO_2$ is contacted with the water or the aqueous solution, and the base, especially by bubbling the $CO_2$ in the water or the aqueous solution prior to it being contacted with the base.

The means B is for example an acidification tank, comprising water or an aqueous solution containing all or some of the constituents of an algal culture medium, in which $CO_2$ is contacted with the water or the aqueous solution, especially by bubbling the $CO_2$ in the water or the aqueous solution.

In accordance with an advantageous embodiment, the invention relates to a device as defined above, in which the culture system is a closed system.0

The term "closed culture system" means a culture area that is isolated from its external environment, for example by a transparent material so as to allow light to pass through. This system makes it possible to better control the culture conditions, and especially the supply of carbon, and to prevent external contamination by other organisms. This leads ultimately to an increased productivity of a biomass and improved quality.

In accordance with an advantageous embodiment, the invention relates to a device as defined above, in which the culture system is an open system.

The term "open culture system" means a culture system open to the ambient environment. The benefit is that it is a less costly system compared to closed systems.

In accordance with an advantageous embodiment, the invention relates to a device as defined above, in which the means A is equipped with a pH and/or temperature probe.

In accordance with an advantageous embodiment, the invention relates to a device as defined above, in which the means A is equipped with a pressure sensor and with a back-pressure regulator.

In accordance with an advantageous embodiment, the invention relates to a device as defined above, in which the means A is equipped with a system making it possible to form bubbles, especially bubbles of controlled size, more particularly bubbles of an average size between 10 µm and 50 µm, from the $CO_2$ produced by the $CO_2$ source.

The formation of small bubbles, in the micrometre range, has the advantage of increasing the contact area with the means A and thus improving the transfer of $CO_2$.

In accordance with an advantageous embodiment, the invention relates to a device as defined above, in which the means B is equipped with a system allowing the formation of bubbles, especially bubbles of controlled size, more particularly bubbles of an average size between 10 µm and 50 µm, from the $CO_2$ produced by the $CO_2$ source.

The formation of small bubbles, in the micrometre range, has the advantage of increasing the contact area with the means B and thus improving the transfer of $CO_2$.

In accordance with an advantageous embodiment, the invention relates to a device as defined above, in which the means A and B are equipped with a liquid outlet and a gas outlet, said outlets being such that:
the liquid outlets of the means A and B supply the culture system with first and second aqueous compositions, respectively;
the gas outlet of the means A is connected to the means B;
the gas outlet of the means B is connected to the culture system.

Thus, in accordance with this embodiment, the surplus flue gases are advantageously injected into the culture system, after having passed through the means B.

In accordance with a particular embodiment, the invention relates to a device as defined above, in which said $CO_2$ source is directly connected to the means A and B, and the means A and B are equipped with a liquid outlet and a gas outlet, the gas outlet of the means A being connected especially to the means B.

In accordance with a particular embodiment, the invention relates to a device as defined above, in which said $CO_2$ source is directly connected to the means A, and the means A and B are equipped with a liquid outlet and a gas outlet, the gas outlet of the means A being connected to the means B.

In accordance with an advantageous embodiment, the invention relates to a device as defined above, in which the $CO_2$ source is discontinuous, and the automaton acts on the various valves connecting said culture system, the first aqueous composition having a pH greater than $pH_H$ and the second composition having a pH lower than $pH_B$, such that:
when the $CO_2$ source produces $CO_2$:
$CO_2$ is directed into the means A so as to obtain a first aqueous composition having a pH greater than $pH_H$, and into the means B so as to obtain a second aqueous composition having a pH lower than $pH_B$;
(if desired) $CO_2$ is directed directly into the culture system if the pH is such that $pH_B<pH<pH_H$;
when the pH of said culture medium reaches an upper limit, $pH_H$, $CO_2$ produced by said source and possibly the second aqueous composition originating from the means B are added to said culture medium so as to lower the pH, preferably until the pH of said culture medium reaches a lower limit, $pH_B$;
when the pH of said culture medium reaches said lower limit, $pH_B$, the first aqueous composition originating from the means A is added to said culture medium so as to raise the pH, preferably until the pH of said culture medium reaches an intermediate value, $pH_I$, with $pH_B<pH_I<pH_H$;
when the $CO_2$ source does not produce $CO_2$:
the first aqueous composition originating from the means A is added to said culture medium so as to supply dissolved carbon to said culture medium, resulting in an increase of the pH until preferably the pH of said culture medium reaches an intermediate value, $pH_I$, with $pH_B<pH_I<pH_H$;
when the pH of said culture medium reaches an upper limit, $pH_H$, the second aqueous composition originating from the means B is added to said culture medium so as to lower the pH, preferably until the pH of said culture medium reaches a lower limit, $pH_B$.

The two actions described when the $CO_2$ source does not produce $CO_2$ can be swapped. In other words, there is generally no defined order. Moreover, these actions can be repeated as necessary.

In accordance with an advantageous embodiment, when the $CO_2$ source does not produce $CO_2$:
the first aqueous composition originating from the means A is added to said culture medium so as to supply dissolved carbon to said culture medium, resulting in an increase of the pH until preferably the pH of said culture medium reaches an intermediate value, $pH_I$, with $pH_B<pH_I<pH_H$; then
when the pH of said culture medium reaches an upper limit, $pH_H$, the second aqueous composition originating from the means B is added to said culture medium so as to lower the pH, preferably until the pH of said culture medium reaches a lower limit, $pH_B$.

Especially, between the two actions mentioned above, the pH rises, especially from $pH_I$ to $pH_H$ due to the consumption of dissolved carbon in the culture medium by the photosynthetic organisms currently growing.

In accordance with an advantageous embodiment, when the $CO_2$ source does not produce $CO_2$:
when the pH of said culture medium reaches an upper limit, $pH_H$, the second aqueous composition originating from the means B is added to said culture medium so as to lower the pH, preferably until the pH of said culture medium reaches a lower limit, $pH_B$; then the first aqueous composition originating from the means A is added to said culture medium so as to supply dissolved carbon to said culture medium, resulting in an increase of the pH until preferably the pH of said culture medium reaches an intermediate value, $pH_I$, with $pH_B<pH_I<pH_H$.

Especially, the pH rises prior to the first action mentioned above, up to $pH_H$, due to the consumption of dissolved carbon in the culture medium by the photosynthetic organisms currently growing. The first and second actions then follow.

FIGURES

FIG. 1 shows a device according to the present invention.

The carbonation tank (2) is fed by a flue gas that is rich in $CO_2$ (1). The gas-liquid transfer is assured either by simple contact between the gaseous environment and the liquid, or by a device allowing the generation of bubbles of small size in order to increase the transfer (21). The pressure within the vessel is a variable that makes it possible to adjust the partial pressure in the tank. In order to optimise the operation of the tank (2), said tank can be equipped with a pH/T probe (22), a pressure sensor (23), a back-pressure regulator (24), a relief valve (25) and a level sensor (26), which controls the intake of the liquid to be carbonated (27). A double jacket (28) can be added in order to assure the regulation of the temperature of the carbonation tank. The use of a centrifugal pump (29) connected to a basic solution makes it possible to produce a concentration of dissolved inorganic carbon in the carbonation solution in accordance with the setpoint pH value and the $CO_2$ composition of the gas at the inlet.

The acidification tank is based on the same principle as the carbonation tank, with a gas-liquid transfer by simple contact, or improved transfer by a device allowing the generation of bubbles of small size (31). The tank can contain a relief valve (32) and a level sensor (33) controlling the intake of the liquid to be acidified (34). The tank is fed directly with gas by the flue gas (1) and/or by the gas outlet of the carbonation tank (2) in order to maximise the utilisation of the flue gas (1).

In addition to the elements necessary for conventional operation of a photobioreactor, the element (4) has inlets for gas (41) and carbonated liquid (42), a vent (43), and a relief valve (44) in the case of a closed system.

The carbonation tank (2) and acidification tank (3) are connected to the photobioreactor (4) by:
 a gas network making it possible to supply flue gas (1) independently to the elements (2), (3) and (4) of the process depending on the control parameters;
 a carbonated liquid network making it possible to supply acidic or basic solution to the photobioreactor (4) depending on the needs of the photobioreactor (4) by means of a centrifugal pump (11).

The automaton controls the operation of the solenoid valves depending on the pH value detected in the photobioreactor (4) and the availability of flue gas (1). The automation of the carbonation tank (2) is also assured by the automaton.

The carbonation tank and acidification tank are regulated via the automaton on the basis of the measurement of the pH in the culture system. In fact, the carbonation is favoured at basic pH, and the biological consumption of the carbon in the reactor also tends to basify the medium. The 2 tanks/liquid solutions are thus associated with a specific regulation method based on the measurement of the pH in the culture system so as to both provide the dissolved carbon in a quantity sufficient for growth and so as to maintain the pH optimum for growth. This is based on the determination of 2 pH setpoints (upper setpoint $pH_H$ and lower setpoint $pH_B$) flanking the optimal value for growth ($pH_I$). Ultimately, the following is thus given $pH_B<pH_I<pH_H$.

Due to the fact that the consumption of the dissolved carbon by the photosynthetic growth results in a rise of the pH in the culture system, when the upper setpoint $pH_H$ is reached, the acidic solution is injected until the lower setpoint $pH_B$ is reached.

When the lower setpoint $pH_B$ is reached, the carbonated solution (basic, $pH>pH_I$) is injected until the pH optimum for growth is reached.

The consumption of the dissolved carbon causes a basification of the medium until the upper setpoint $pH_H$ is reached, leading to a repetition of the cycle.

It should be noted that the setpoints $pH_B$ and $pH_H$ can be selected to be very close to $pH_I$, ultimately making it possible to hold the pH at a level optimum for growth.

EXAMPLE

The $CO_2$ source is an industrial flue gas comprising 9% $CO_2$.

The first and second aqueous compositions in the carbonation and acidification tanks respectively, are at a temperature of 25° C.

In the carbonation tank, the pH and the concentration of DIC of the first aqueous composition are related as indicated in the following table:

| pH | DIC (mM) |
| --- | --- |
| 7.5 | 46.7 |
| 8 | 141.2 |
| 8.5 | 444.1 |
| 9 | 1441.2 |

Thus, the addition of a base, especially a strong base, makes it possible to increase the concentration of DIC of the first aqueous composition, and therefore the amount of DIC stored in the carbonation tank.

In the acidification tank, the pH of the second aqueous composition, at equilibrium, is 4.42 and the concentration of DIC is 3 mM.

The invention claimed is:

1. A method for the culture of photosynthetic organisms, in which a first aqueous composition having a pH greater than $PH_H$ and of a second composition having a pH lower than $pH_B$ is used, said method comprising:
 culturing the photosynthetic organisms in a culture system comprising a culture medium, wherein the photosynthetic organisms are selected from the group consisting of microalgae, cyanobacteria and macroalgae;
 obtaining said first aqueous composition having a pH greater than $pH_H$ by contacting $CO_2$ produced by a continuous or discontinuous $CO_2$ source, a base, and water;
 obtaining said second aqueous composition having a pH lower than $pH_B$ by dissolving $CO_2$ produced by said source in water;
 wherein the pH of said culture medium is such that:

when the pH of said culture medium reaches an upper limit, $pH_H$, adding the second aqueous composition and/or $CO_2$ produced by said source, to said culture medium so as to lower the pH, until the pH of said culture medium reaches a lower limit, $pH_B$;

when the pH of said culture medium reaches said lower limit, $pH_B$, adding the first aqueous composition to said culture medium so as to increase the pH, until the pH of said culture medium reaches an intermediate value, $pH_I$, with $pH_B < pH_I < pH_H$;

when the pH of said culture medium is lower than $pH_H$, and lower than $pH_I$, optionally adding the first aqueous composition to said culture medium so as to increase the pH, until the pH of said culture medium reaches the intermediate value $pH_I$, wherein in the first aqueous composition, the dissolved inorganic carbon (DIC) is predominantly in the form of carbonate ions and bicarbonate ions, said DIC is between 45 and 1450 mM, and wherein in the second aqueous composition, the dissolved inorganic carbon (DIC) is predominantly in the form of carbonic acid.

2. The method according to claim 1, wherein the first aqueous composition has a pH comprised between 7.5 and 9, and wherein the second composition has a pH comprised between 4 and 5.

3. A method according to claim 1, wherein the photosynthetic organisms are selected from the group consisting of:

microalgae, selected from the group consisting of the genera *Chlorella, Nannochloropsis, Chlamydomonas, Tetraselmis, Scendesmus, Parachlorella, Porphyridium, Botryococcus* and *Neochloris*;

cyanobacteria, selected from the group consisting of the genera *Arthrospira, Aphazomenon* and *Synechocystis*; and macroalgae, selected from the group consisting of Ulva, Fucus, and Palmaria.

4. A method according to claim 1, wherein the $CO_2$ source is formed by industrial flue gases, said $CO_2$ source being selected from the group consisting of emissions from boilers, thermal power plants, cement plants, metallurgical plants, refineries, factories manufacturing ammonia, fermentation processes, and anaerobic digestion processes.

5. A method according to claim 1, wherein the $CO_2$ source is discontinuous and the automaton acts on the various valves connecting a system for the culture of photosynthetic organisms comprising said culture medium, the first aqueous composition having a pH greater than $pH_H$ and the second composition having a pH lower than $pH_B$, said method comprising when the $CO_2$ source produces $CO_2$:

obtaining in the presence of a base, said first aqueous composition, by directing $CO_2$ into water or an aqueous solution containing all or some of the constituents of an algal culture medium, and obtaining said second aqueous composition by directing $CO_2$ into water or an aqueous solution containing all or some of the constituents of an algal culture medium and by dissolving $CO_2$ produced by said source in the water or the aqueous solution;

directing $CO_2$ directly into the culture system if the pH is such that $pH_B < pH < pH_H$;

adding $CO_2$ produced by said source and by the second aqueous composition when the pH of said culture medium reaches an upper limit, $pH_H$, to said culture medium so as to lower the pH, until the pH of said culture medium reaches a lower limit, $pH_B$;

no longer adding the $CO_2$ produced by said source to said culture medium when the pH of said culture medium reaches said lower limit, $pH_B$, and adding the first aqueous composition to said culture medium so as to raise the pH, until the pH of said culture medium reaches an intermediate value, $pH_I$, with $pH_B < pH_I < pH_H$;

when the $CO_2$ source does not produce $CO_2$:

adding the first aqueous composition to the culture medium so as to supply dissolved carbon to said culture medium, resulting in an increase of the pH until the pH of said culture medium reaches an intermediate value, $pH_I$, with $pH_B < pH_I < pH_H$;

adding the second aqueous composition, when the pH of said culture medium reaches an upper limit, $pH_H$, to said culture medium so as to lower the pH, until the pH of said culture medium reaches a lower limit, $pH_B$.

6. A method according to claim 1, wherein the culture system is a closed system.

7. A method for the culture of photosynthetic organisms, using a continuous or discontinuous $CO_2$ source, in which the $CO_2$ is directed by means of pipes and valves controlled by an automaton:

in a culture system comprising a medium for the culture of photosynthetic organisms; or in water or an aqueous solution containing all or some of the constituents of an algal culture medium so as to obtain, in the presence of a base, a first aqueous composition having a pH greater than $pH_H$; or in water or an aqueous solution containing all or some of the constituents of an algal culture medium so as to obtain a second aqueous composition having a pH lower than $pH_B$, by dissolving $CO_2$ produced by said source in water;

said method comprising culturing the photosynthetic organisms in a culture system comprising a culture medium, wherein the photosynthetic organisms are selected from the group consisting of microalgae, cyanobacteria and macroalgae, using the $CO_2$ originating from said source and the carbonate ions and the carbonic acid respectively contained in the first and second aqueous compositions, obtaining a biomass of photosynthetic organisms, by culturing the photosynthetic organisms, and i. when the pH of said culture medium reaches an upper limit $pH_H$, adding the second aqueous composition and/or the $CO_2$ produced by said source to said culture medium in order to lower the pH, until the pH of said culture medium reaches a lower limit, $pH_B$;

ii. when the pH of said culture medium reaches said lower limit, $pH_B$, adding the first aqueous composition to said culture medium so as to increase the pH, until the pH of said culture medium reaches an intermediate value, $pH_I$, with $pH_B < pH_I < pH_H$;

iii. when the pH of said culture medium is lower than $pH_H$, and lower than $pH_I$, adding the first aqueous composition to said culture medium so as to increase the pH, until the pH of said culture medium reaches the intermediate value $pH_I$;
said value of $pH_I$ being between 6 and 10 in the culture medium;
said $pH_H$ being such that $pH_H = pH_I + x$ in the culture medium, x being between 0.02 and 1.5;
said $pH_B$ being such that $pH_B = pH_I - y$ in the culture medium, y being between 0.02 and 1.5;
said base being selected from the group composed of sodium hydroxide and potassium hydroxide;
said culture medium being at a temperature between 15° C. and 35° C.,
wherein in the first aqueous composition, the dissolved inorganic carbon (DIC) is predominantly in the form of carbonate ions and bicarbonate ions, said DIC is between 45 and 1450 mM,
and
wherein in the second aqueous composition, the dissolved inorganic carbon (DIC) is predominantly in the form of carbonic acid.

8. A method according to claim 7, wherein the photosynthetic organisms are selected from the group consisting of:
microalgae, selected from the group consisting of the genera *Chlorella, Nannochloropsis, Chlamydomonas, Tetraselmis, Scendesmus, Parachlorella, Porphyridium, Botryococcus* and *Neochloris*;
cyanobacteria, selected from the group consisting of the genera *Arthrospira, Aphazomenon* and *Synechocystis*; and
macroalgae, selected from the group consisting of Ulva, Fucus, and Palmaria.

9. A method according to claim 7, wherein the $CO_2$ source is formed by industrial flue gases, said $CO_2$ source being selected from the group consisting of emissions from boilers, thermal power plants, cement plants, metallurgical plants, refineries, factories manufacturing ammonia, fermentation processes, and anaerobic digestion processes.

10. A method according to claim 7, wherein the $CO_2$ source is discontinuous and the automaton acts on the various valves connecting a system for the culture of photosynthetic organisms comprising said culture medium, the first aqueous composition having a pH greater than $pH_H$ and the second composition having a pH lower than $pH_B$, said method comprising
when the $CO_2$ source produces $CO_2$:
obtaining in the presence of a base, said first aqueous composition, by directing $CO_2$ into water or an aqueous solution containing all or some of the constituents of an algal culture medium, and
obtaining said second aqueous composition by directing $CO_2$ into water or an aqueous solution containing all or some of the constituents of an algal culture medium and by dissolving $CO_2$ produced by said source in the water or the aqueous solution;
directing $CO_2$ directly into the culture system if the pH is such that $pH_B < pH < pH_H$;
adding $CO_2$ produced by said source and by the second aqueous composition when the pH of said culture medium reaches an upper limit, $pH_H$, to said culture medium so as to lower the pH, until the pH of said culture medium reaches a lower limit, $pH_B$;
no longer adding the $CO_2$ produced by said source to said culture medium when the pH of said culture medium reaches said lower limit, $pH_B$, and adding the first aqueous composition to said culture medium so as to raise the pH, until the pH of said culture medium reaches an intermediate value, $pH_I$, with $pH_B < pH_I < pH_H$;
when the $CO_2$ source does not produce $CO_2$:
adding the first aqueous composition to the culture medium so as to supply dissolved carbon to said culture medium, resulting in an increase of the pH until the pH of said culture medium reaches an intermediate value, $pH_I$, with $pH_B < pH_I < pH_H$;
adding the second aqueous composition, when the pH of said culture medium reaches an upper limit, $pH_H$, to said culture medium so as to lower the pH, until the pH of said culture medium reaches a lower limit, $pH_B$.

11. A method according to claim 7, wherein the culture system is a closed system.

12. A method according to claim 7, wherein the culture system is an open system.

\* \* \* \* \*